(12) United States Patent
Kim et al.

(10) Patent No.: US 7,780,848 B2
(45) Date of Patent: Aug. 24, 2010

(54) APPARATUS FOR BLOOD DIALYSIS AND FILTRATION

(75) Inventors: Sung-Teh Kim, Kitakyushu (JP);
Kunihiko Yamanaka, Hiroshima (JP);
Naritomi Maeda, Hiroshima (JP);
Katsunori Masaoka, Hiroshima (JP);
Kayoko Segawa, Kitakyushu (JP);
Chieko Yamamoto, Kitakyushu (JP)

(73) Assignee: JMS Co., Hiroshima (JP)

( * ) Notice: Subject to any disclaimer, the term of this patent is extended or adjusted under 35 U.S.C. 154(b) by 1144 days.

(21) Appl. No.: 10/561,110

(22) PCT Filed: Jun. 18, 2004

(86) PCT No.: PCT/JP2004/008938

§ 371 (c)(1),
(2), (4) Date: Dec. 15, 2005

(87) PCT Pub. No.: WO2004/112870

PCT Pub. Date: Dec. 29, 2004

(65) Prior Publication Data

US 2006/0138049 A1    Jun. 29, 2006

(30) Foreign Application Priority Data

Jun. 19, 2003    (JP)    ............................. 2003-175601

(51) Int. Cl.
*A61M 1/30* (2006.01)

(52) U.S. Cl. .................... 210/138; 210/141; 210/321.6; 604/5.01; 604/6.11; 604/6.16

(58) Field of Classification Search ................ 210/646, 210/138, 141, 321.6; 604/5.01, 6.11, 6.16
See application file for complete search history.

(56) References Cited

U.S. PATENT DOCUMENTS

| 4,599,165 | A | 7/1986 | Chevallet |
| 6,626,857 | B1 * | 9/2003 | Ohta et al. ................. 604/6.13 |
| 7,201,730 | B2 * | 4/2007 | Davidner et al. ........... 604/6.08 |
| 2003/0163077 | A1 | 8/2003 | Kim et al. |

FOREIGN PATENT DOCUMENTS

| JP | 6-114102 | 4/1994 |
| JP | 6-134031 | 5/1994 |
| JP | 7-313589 | 12/1995 |
| JP | 2002-325837 | 11/2002 |

* cited by examiner

*Primary Examiner*—Terry K Cecil
(74) *Attorney, Agent, or Firm*—Jordan and Hamburg LLP

(57) ABSTRACT

A single needle hemodiafiltration apparatus is provided. The single needle hemodiafiltration apparatus includes circuits for blood supply from a patient and blood return to a patient, a dialysis fluid supply system for supplying a dialysis fluid, and a system for controlling the blood flow and dialysis fluid flow in a separation device which is equipped to perform filtration and back-filtration operations. A controller is provided that controls, in a series of coordinated operations, the flow of blood from the patient into the separation device, the flow of filtration fluid and back filtration fluid, and the return of blood to the patient.

17 Claims, 5 Drawing Sheets

APPARATUS FOR BLOOD DIALYSIS AND FILTRATION

TECHNICAL FIELD

The present invention relates to a hemodiafiltration apparatus for purifying blood by making use of extracorporeal circulation as treatment for substituting for the function of the kidney of a patient suffering from chronic renal failure in the medical field.

BACKGROUND ART

For the treatment of a patient suffering from renal failure, there have been proposed various blood purifying methods in which blood is taken out from the body of the patient to be purified and is returned into the body. To purify the blood, hemodialyzers which accommodate a porous membrane (hereinafter also referred to as "dialysis membrane") such as a hollow yarn cellulose membrane, polyacrylonitrile membrane or polysulfone membrane in the housing are generally used. The purification method to be employed differs according to the state of the disease and the conditions of a patient.

For example, in the case of hemodialysis (HD), blood and a dialysis fluid are contacted with each other through the dialysis membrane of a hemodialyzer to remove urotoxin such as urea and uric acid accumulated in the blood of a patient by the movement of substances caused by diffusion. In the case of hemofiltration (HF), water, body wastes and toxins contained in the blood are removed by filtration through holes open in a porous membrane.

In the above treatment method, HD (hemodialysis) is excellent in the removal of small-molecular wastes and solutes but is inferior in the removal of medium molecules and large molecules. Therefore, it is known that when HD is continued for a longtime, the development of a complication such as secondary dialysis-related amyloidosis or trophopathy cannot be suppressed. Meanwhile, HF (hemofiltration) is excellent in the removal of medium and large molecular wastes but is inferior in the removal of small molecules. Therefore, it is considered as unsuitable for long-term treatment since toxin such as urea is accumulated in the body.

As a treatment method having the advantages of both HD and HF, that is, well-balanced removal efficiency for small to large molecules, there has been proposed hemodiafiltration (HDF). However, since filtration and fluid substitution operations have been complicated in the clinical scene and restrictions have been placed on the use of a bottle preparation of an expensive substitution fluid by medical economy, a small amount, for example, 5 to 10 liters of a substitution fluid has been used. Therefore, the excellent removal characteristics of HDF could not be obtained fully and a marked clinical effect did not appear. Recently, to eliminate a shortage of a substitution fluid, on-line HDF method in the broad sense which is a new technique capable of large-quantity filtration and large-quantity fluid substitution has been established by using a purified dialysis fluid as a substitution fluid for filtration. The technology as shown, for example, by JP-A 6-134031 and JP-A 7-313589 as prior art documents is disclosed.

HD, HF and HDF are treatment methods making use of a removing apparatus which is installed halfway in extracorporeal circulation, for taking out the blood of a patient to the outside of the patient's body and recirculating it into the body. Therefore, to maintain extracorporeal circulation, an extracorporeal circulation circuit (also referred to as "blood circuit") is used, one end of the blood circuit is connected to a puncture needle on the arterial side which is introduced into the blood vessel of a patient to extract the blood (blood extraction), and the other end of the blood circuit is connected to a puncture needle on the venous side which is introduced into the blood vessel of the patient to return the blood into the body of the patient (blood reinfusion). That is, blood access operation for introducing the two puncture needles is required to maintain extracorporeal circulation.

However, since the blood vessel is thin and fragile, there is a case where it is difficult to leave the two indwelling needles on the arterial and venous sides. In the current situation where the number of old dialysis patients is increasing, the number of cases where this blood access is difficult is increasing each year. For the cases where blood access is difficult, so-called "single-needle HD" in which the extraction of the blood from a patient and the reinfusion of the blood to the patient from the blood circuit are carried out with a single needle alternately and intermittently may be carried out. However, conventional single-needle HD is unsuitable for the long-term treatment of a patient suffering from chronic renal failure as its removal efficiency for urotoxin is extremely low.

The present invention provides a novel single-needle hemodiafiltration apparatus (hereinafter also referred to as "single-needle HDF") which shows a well-balanced excellent removal efficiency for from small to large molecules and realizes the purification of blood by single-needle extracorporeal circulation.

DISCLOSURE OF THE INVENTION

The present invention has solved the above problems by means of the following structure.

That is, the present invention provides a hemodiafiltration apparatus capable of extracorporeal circulation operation using a blood circuit in which blood extraction and reinfusion are performed by using a single needle, that is, one puncture needle, characterized by having the following structure. That is, the hemodiafiltration apparatus is roughly composed of: (1) a blood supply system for supplying blood; (2) a dialysis fluid supply system for supplying a dialysis fluid; and (3) a system for controlling the movement of a fluid between the both supply systems. A blood circulation system has an arterial side blood circuit for extracting blood from a patient and flowing it into a hemodialyzer and a venous side blood circuit for returning blood from the hemodialyzer to the patient, and at least one of the two blood circuits of the blood circulation system has a blood pump which can control the flow rate and can turn in normal and opposite directions. The dialysis fluid supply system has a dialysis fluid supply line for perfusing the hemodialyzer with a dialysis fluid and a dialysis fluid discharge line and the dialysis fluid supply line and the dialysis fluid discharge line has delivery means for supplying a dialysis fluid and delivery means for discharging a dialysis fluid, respectively, one of the dialysis fluid supply line and the dialysis fluid discharge line has at least one or more filtration/back-filtration fluid supply means for carrying out filtration and back-filtration together with the delivery means, which can turn in normal and opposite directions and can control a flow rate, and further has water removing and fluid discharge means. That is, the hemodiafiltration apparatus has: a blood extracting mechanism (blood extracting process) for extracting blood into the blood circuit by flowing out a fluid in the blood circuit to a dialysis fluid circuit side by filtration through a hemodialyzer accommodating a hollow yarn membrane; and a reinfusion mechanism (reinfusion process) for returning the blood in the blood circuit to the patient by flowing the dialysis fluid from the dialysis fluid circuit side to the blood circuit side by forced back-filtration through the hemodialyzer, and is characterized in that hemodiafiltration apparatus includes a mechanism capable of repeating intermittently and at least a plurality of times an operation of flowing out a fluid from the blood circuit side to the dialysis fluid circuit side by the filtration (hereinafter also referred to as "filtration" or "blood extraction") and an operation of flowing the fluid into the blood circuit side from the dialysis fluid side by back-filtration (also referred to as "back-filtration" or "reinfusion").

That is, the present invention provides a single-needle hemodiafiltration apparatus in which a hemodialyzer accommodating a hollow yarn membrane is used to carry out the step of returning blood by forced back-filtration through the hemodialyzer so as to flow a dialysis fluid into a blood circuit from a dialysis fluid circuit and to carry out the step of removing blood by filtration through the hemodialyzer so as to flow out the fluid in the blood circuit to the dialysis fluid circuit, characterized in that the operation of flowing the fluid into the blood circuit from the dialysis fluid side by the back-filtration (hereinafter also referred to as "back-filtration operation") and the operation of flowing out the fluid from the blood circuit to the dialysis fluid circuit by the filtration (hereinafter also referred to as "filtration operation") are repeated intermittently and a plurality of times at least automatically.

In the single-needle hemodiafiltration apparatus of the present invention, as the total amount of the circulating blood per one time of treatment can be increased as compared with typical single-needle hemodialysis, the removal efficiency by diffusion is improved. Further, the filtration effect of HDF can be obtained, thereby making it possible to achieve efficient removal of small to large molecular urotoxin with single-needle extracorporeal circulation.

BEST MODE FOR CARRYING OUT THE INVENTION

Figure 1:
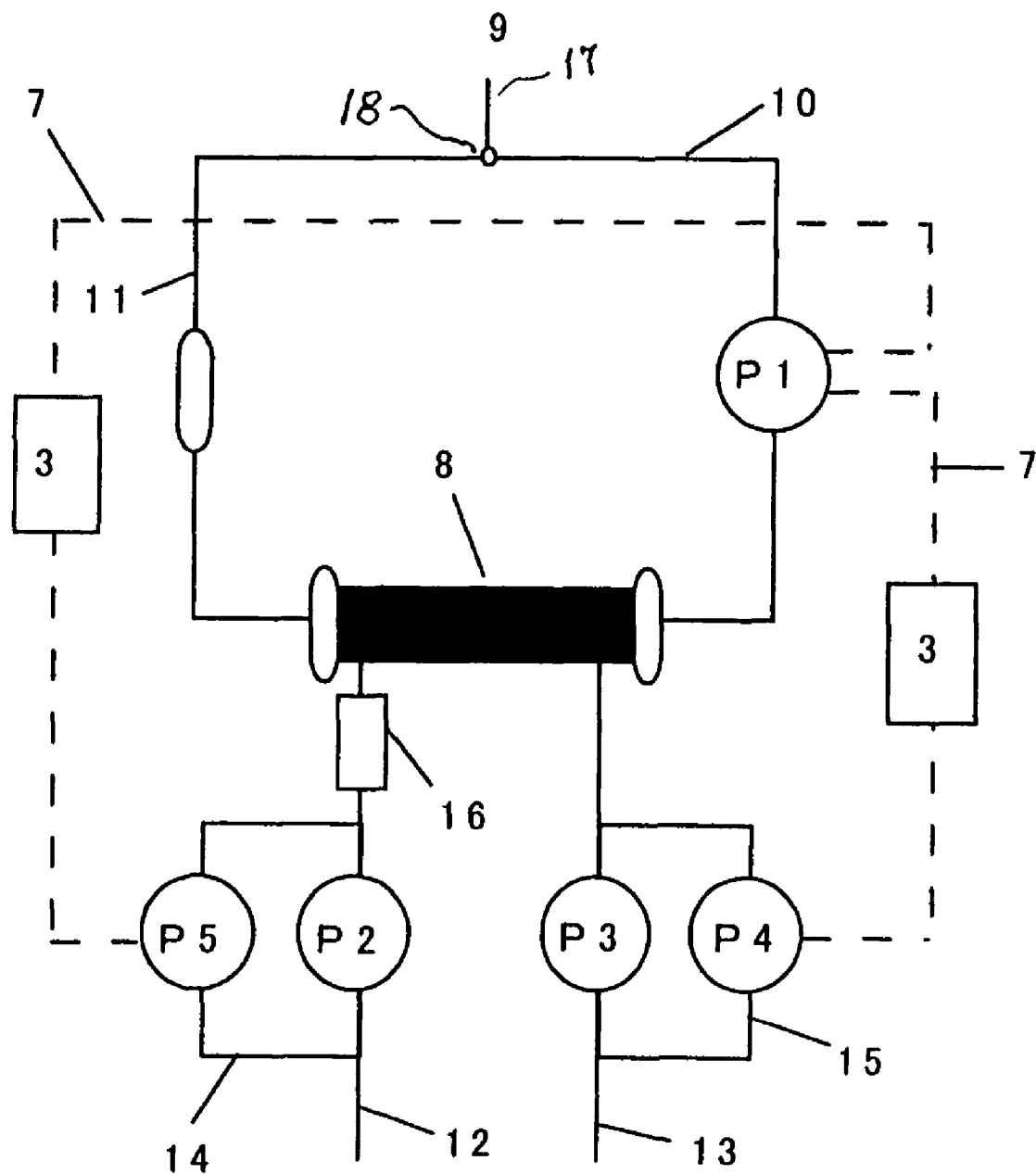
FIG. 1 is a schematic diagram of a hemodiafiltration apparatus as a whole according to an example of the present invention.

A hemodiafiltration apparatus of the present invention is capable of arbitrarily adjusting filtration/back-filtration conditions for each cycle while retaining a basic feature of carrying out HDF making use of a single-needle exclusive extracorporeal circulation circuit. The amount of filtration (i.e., the amount of the removed blood) and the amount of back-filtration (i.e., the amount of the returned blood) per cycle are kept equal to each other. By controlling filtration/back-filtration fluid supply means and a blood pump in an associated manner, optimum filtration/back-filtration conditions can be selected and solutes can be removed efficiently. As general characteristics, the removal efficiency of small molecules becomes higher as the total amount of blood supplied into a hemodialyzer during the working time (almost equal to the total amount of the removed blood) increases and the removal efficiency of large molecules becomes higher as the volume of filtration or back-filtration of each cycle increases. Since the main drive force for blood extraction is filtration, the total amount of the blood supplied into the hemodialyzer depends on the total amount of filtration. In a filtration phase, the blood is purified by filtration and diffusion and in a blank phase where the blood circulates, the blood is purified by diffusion. Meanwhile, as the back-filtration phase mainly aims at fluid substitution for supplementing the loss of the body fluid caused by the reinfusion of the blood and filtration, it does not contribute to the purification of the blood much. Therefore, in order to enhance the blood purification efficiency of the single-needle HDF of the present invention, as for time apportionment among phases in one cycle, how the back-filtration phase is completed quickly is an important point. Various embodiment modes and significance of the single-needle HDF of the present invention will be described hereinbelow.

A blank time when filtration and back-filtration operations are not carried out is interposed between the filtration phase and the subsequent back-filtration phase and the step of circulating blood in extracorporeal circulation is carried out during this blank time, whereby blood extracted into the extracorporeal circulation circuit (blood circuit) is dialyzed with a dialysis fluid in the blood purifying apparatus and the water removal step is carried out by activating a water removing pump. In the single-needle HDF of the present invention, the dialysis fluid is refluxed to the blood purifying apparatus even in the blank phase. By providing the blank phase right after the filtration phase, filtration conditions are set excessively in the filtration phase so that if a predetermined filtration unit amount is not achieved during the filtration phase, the remaining portion not filtered is filtered in the blank phase by activating the water removing pump, thereby exhibiting a complementary function of the filtration phase. The blank time during which filtration and back-filtration operations are not carried out is interposed between the back-filtration phase and the subsequent filtration phase and the step of circulating blood in extracorporeal circulation is carried out during this period of time, or this operation is automatically repeated, so as to prevent the blood which has been filtered, dialyzed and purified with the supply of the fluid in the blood purifying apparatus from being filtered again. The blank time has the effect of eliminating a dead space phenomenon that the fluid in the membrane of the blood purifying apparatus goes back and forth as well. Further, it also has the effect of eliminating a refiltration phenomenon that the dialysis fluid supplied into the hemodialyzer or the blood circuit by back-filtration is filtered again before it is fully mixed with blood. Although the blank phase has the above significance, securing the blank phase is not essential to the single-needle HDF of the present invention.

In the single-needle HDF of the present invention, the blood extraction step of extracting the blood from the body of a patient is carried out through the interaction of the filtration/back-filtration means and the blood pump. When the fluid (blood, dialysis fluid or a mixture thereof) in the blood circuit is to be filtered, various blood extraction patterns can be realized according to the relationship between the filtration rate and the fluid supply rate of the blood pump which turns in the normal direction (blood flow rate). For example, when they are equal to each other, the blood is removed only through the branch of the blood circuit on the blood pump side. When the filtration rate is higher than the blood flow rate, the blood is removed through the branch of the blood circuit on the blood pump side based on the flow rate of the blood pump and the amount of the blood corresponding to a difference between the filtration rate and the blood flow rate is removed through the branch of the blood circuit on the side with no blood pump. When the blood flow rate is higher than the filtration rate, the blood is removed through the branch of the blood circuit on the blood pump side at a flow rate equal to the filtration rate and the fluid in the blood circuit is re-circulated in the normal rotation direction of the blood pump at a flow rate corresponding to a difference between the blood flow rate and the filtration rate. When the blood pump is stopped and only filtration is started, the blood is removed only through the branch of the blood circuit on the side with no blood pump. When the blood pump is turned in the opposite direction, the blood is removed from the branch of the blood circuit on the side with no blood pump at a filtration rate and the fluid in the blood circuit is re-circulated in the opposite rotation direction of the blood pump at a flow rate of the blood. The extraction of the blood from the branch of the blood circuit on the blood pump side, the extraction of the blood from the branch of the blood circuit on the side with no blood pump, the extraction of the blood from the both branches, or the extraction of the blood from the branch on one side of the blood circuit while the fluid is re-circulated becomes possible as described above.

In the single-needle HDF of the present invention, the circulation of the blood in the blood circuit has a function of purifying the blood in the blood circuit by dialysis (diffusion phenomenon) in the hemodialyzer. Although a diffusion phenomenon occurs regardless of the operation state of filtration which is carried out simultaneously, when high-speed back-filtration is started, the purification efficiency of the blood by diffusion partially lowers. It is possible to add the operation of removing the blood by filtration or the operation of returning the blood by back-filtration while the fluid in the blood circuit is re-circulated. In this case, part of the fluid in the blood circuit is replaced by the blood extracted from the body successively. The clearance of the removal of substances by diffusion in the (re-)circulation process is limited by the average rate at which the fluid in the blood circuit is replaced with the extracted blood by filtration/back-filtration rather than the circulation rate of the blood pump.

In the single-needle HDF of the present invention, the timing of carrying out the water removal step for correcting an excess of the body fluid in the cycle can be arbitrarily selected. For example, the step can be continued equally over the whole working time. Alternatively, the removal of water can be carried out by selecting a desired number of phases from one or more filtration phases, one or more back-filtration phases, and 0, one, or more blank phases. When the removal of water is not necessary, the removal of water is nil and only filtration/back-filtration are started. The above system is for removing water equally in each cycle. The amount of the removed water per cycle can be changed with the passage of time based on the preset profile. For example, the amount of the removed water per cycle over the working time is automatically calculated so that while the amount of the removed water per cycle is reduced linearly or along an asymptote at a desired rate from the beginning to the end, the set total amount of the removed water is attained. The removal of water for correcting an excess of the body fluid rarely affects the efficiency of diffusion.

In a mechanism in which the filtration/back-filtration fluid supply means and the water removing and fluid discharge means are separate from each other, when the water removing and fluid discharge means is activated independently, the removal of water is carried out independently regardless of the filtration/back-filtration pattern. When the apparatus comprises multifunctional filtration control means which serves as two fluid supply means, the fluid supply rate in the fluid discharge direction (normal direction) of the control means is increased by the water removing rate, whereby the removal of water is carried out independently regardless of the filtration/back-filtration pattern.

The reinfusion step of returning the blood into the body of the patient in the single-needle HDF of the present invention is carried out through the interaction of the filtration/back-filtration fluid supply means and the blood pump. When the fluid is to be reversely filtered into the blood circuit through the hemodialyzer, various blood reinfusion patterns can be realized according to the relationship between the back-filtration rate and the fluid supply rate of the blood pump which is turned in the opposite direction (blood flow rate). For example, when they are equal to each other, the blood is returned only through the branch of the blood circuit on the blood pump side. When the back-filtration rate is higher than the blood flow rate, the blood is returned through the branch of the blood circuit on the blood pump side based on the flow rate of the blood pump and the amount of the blood corresponding to a difference between the back-filtration rate and the blood flow rate is returned through the branch of the blood circuit on the side with no blood pump. When the blood flow rate is higher than the back-filtration rate, the blood is returned through the branch of the blood circuit on the blood pump side at a flow rate equal to the back-filtration rate and the fluid in the blood circuit is re-circulated in the opposite rotation direction of the blood pump at a flow rate corresponding to a difference between the blood flow rate and the back-filtration rate. When the blood pump is stopped and only back-filtration is started, the blood is returned only through the branch of the blood circuit on the side with no blood pump. When the blood pump is turned in the normal direction, the blood is returned from the branch of the blood circuit on the side with no blood pump at a back-filtration rate and the fluid in the blood circuit is re-circulated in the normal rotation direction of the blood pump at a flow rate of the blood. The reinfusion of the blood from the branch of the blood circuit on the blood pump side, the reinfusion of the blood from the branch of the blood circuit on the side with no blood pump, the reinfusion of the blood from the both branches, or the reinfusion of the blood from one branch of the blood circuit while the fluid is re-circulated becomes possible as described above.

The hemodiafiltration apparatus having polyfunctional filtration control means has one fluid supply means which can turn in normal and opposite directions in either one of a dialysis fluid supply line for supplying the dialysis fluid to the hemodialyzer and a dialysis fluid discharge line in place of the above filtration/back-filtration fluid supply means and the water removing and fluid discharge means to set the filtration/back-filtration rate and the times of the filtration phase, the back-filtration phase and the blank phase to desired values so as to carry out the above filtration/back-filtration and water removal. The apparatus has an advantage that its structure and control are simplified while it has the same function as the above hemodiafiltration apparatus having the filtration/back-filtration fluid supply means and the water removing and fluid discharge means.

In the step of removing water, the capacity of the blood circuit which has been reduced by the movement of the fluid from the blood circuit to the dialysis fluid side through the hemodialyzer is replenished by extracting the blood from the body in the filtration phase and the blank phase, and is offset by a reduction in the back-filtration rate in the back-filtration phase. A change in the inside pressure of the blood circuit can be partially buffered by this natural offsetting phenomenon.

The movement of the fluid which permeates through the hemodialysis membrane in each cycle is limited by its moving speed and moving time. The amount of filtration by the filtration operation is determined by the product of the filtration rate and the time required for filtration, and the amount of back-filtration by the back-filtration operation is determined by the product of the back-filtration rate and the time required for back-filtration. Therefore, when two factors out of three factors which are amount, rate and time are determined in one time of filtration or back-filtration operation, the value of the remaining one factor is determined. By applying this relationship, the setting and control of a filtration/back-filtration pattern are facilitated.

In the single-needle HDF according to the present invention, the minimum recurring unit which is a combination of desired numbers of filtration phases, back-filtration phases and blank phases, and the order of these phases is defined as one cycle. When the recurring unit simply is composed of one filtration phase and one back-filtration phase, it can be expressed that one cycle starts from the filtration operation and ends before the start of the next filtration operation through at least one back-filtration operation (or starts from the back-filtration operation and ends before the start of the next back-filtration operation through at least one filtration operation). The time of the filtration phase and the time of the back-filtration phase included in each cycle do not need to be the same. In general, to improve the removal efficiency, the time of the back-filtration phase is set shorter than the time of the filtration phase. In this case, the back-filtration rate becomes higher than the filtration rate from the relationship described above.

In the single-needle HDF according to the present invention, the number of the above cycles which are carried out during the hemodialysis operation period can be set to a desired value. In general, before the single-needle HDF is carried out, a filtration/back-filtration pattern which is composed of the phase structure of each cycle, the amount of filtration/back-filtration in each cycle and the flow rate of the blood in each phase is determined, and the same cycle is then repeated over the working time in most cases. However, the structure of each cycle (that is, a combination of the desired numbers of filtration phases, back-filtration phases and blank phases and the order of these phases) may be changed with the passage of time. For example, the time reduction of the amount of filtration/back-filtration (stroke volume) per cycle is extremely useful from the viewpoint of maintaining the circulation of the blood of a patient in extracorporeal circulation.

By setting the working time, the total amount of a substitution fluid, and the number of cycles instead of specifying HDF conditions by determining the phase structure of each cycle and the amount of filtration/back-filtration (stroke volume) per cycle, that is, the filtration/back-filtration pattern, HDF conditions can be easily specified. In this case, the amount of filtration/back-filtration is obtained by dividing the total amount of a substitution fluid by the number of cycles. The absolute time of each phase is actually determined according to the numbers of filtration phases, back-filtration phases and blank phases and the order of these phases registered in advance. It is desired that when the stroke volume per cycle calculated from the above settings exceeds 200 ml, the apparatus should have a mechanism for rejecting it as an improper treatment condition. When the stroke volume exceeds 200 ml, the circulation of the blood of a patient becomes unstable.

In all the possible variations of the single-needle HDF according to the present invention, the amount of the removed water for correcting an excess of the body fluid must be set separately even when the removal of water is not carried out.

In the single-needle HDF according to the present invention, when the above working time or the above number of cycles is not input prior to treatment, the apparatus is manipulated or controlled with an initial value input into an input unit. When the initial value is employed, HDF conditions can be easily specified by inputting the above amount of the removed water and the total amount of the substitution fluid. The initial value may be newly input in place of the value input into the input unit in advance. Although a plurality of initial values customized for each patient may be registered, priority conditions must be specified in advance in this case.

In the single-needle HDF apparatus having multifunctional filtration control means, when the amount of a fluid discharged from a dialysis fluid circuit independently of delivery means for discharging a dialysis fluid is taken as the amount of a fluid discharged by a pump, this amount of the fluid discharged by the pump is controlled to become the sum of the amount of the removed water flowing out from the blood side circuit to the dialysis fluid side circuit by the above water removing step and the amount of filtration (equal to the amount of back-filtration or the amount of the substitution fluid) flowing out from the blood circuit to the dialysis fluid circuit by the above filtration operation. Also in the single-needle HDF apparatus having no multifunctional filtration control means, the amount of the fluid discharged by the pump may be used as a term which means the total of the amount of filtration and the amount of the removed water.

In the single-needle HDF apparatus according to the present invention, the above amount of the fluid discharged by the pump is controlled to become the sum of the amount of the removed water per cycle and the amount of the reversely filtered fluid per cycle in each cycle, a plurality of cycles or the working time.

In the single-needle HDF apparatus according to the present invention, various water removal patterns can be selected according to whether water removal is carried out continuously or only in a specific phase or whether the water removal rate is made constant or changed during the working time. When the water removal rate is made constant in the working time, the amount of the removed water per cycle is obtained by dividing the amount of water removed from a patient by the number of cycles equally and when the time of each cycle differs, the amount of the removed water is calculated from the time ratio (time function). When water removal is carried out only in a specific phase, the water removing rate is obtained by dividing the total amount of the removed water by the integrated time of phases in which water removal is carried out in the working time.

In the single-needle HDF apparatus according to the present invention, when the amount of a fluid filtered by the filtration operation of each cycle is taken as the amount of filtration/back-filtration per cycle, the amount of filtration/back-filtration per cycle is calculated from the product of the filtration rate and the filtration time apportioned to each cycle or from the back-filtration rate and the back-filtration time. When the total amount of filtration, the number of cycles and phase apportionment are determined, a filtration/back-filtration pattern is automatically calculated, set and controlled, thereby making the operation of inputting treatment conditions easy.

In the single-needle HDF apparatus according to the present invention, to input conditions for the filtration/back-filtration pattern for each cycle, the time of each phase and the filtration/back-filtration rate are automatically calculated and set by specifying the amount of the substitution fluid per cycle (stroke volume), the cycle time, the time ratio of the filtration phase to the back-filtration phase and the time of the blank phase.

Stated more specifically, the amount of the substitution fluid per cycle (stroke volume) and the time of filtration (time of the filtration phase) per cycle or the time of back-filtration per cycle (the time of the back-filtration phase) have the following relationships.

[back-filtration rate]=[amount of substitution fluid]÷
  [time of back-filtration]

[filtration rate]=[amount of substitution fluid]÷[time
  of filtration]

The amount of the substitution fluid per cycle (stroke volume), the amount of the removed water per cycle, the amount of the fluid discharged by the pump per cycle, the amount of water removed from a patient, the working time, the number of cycles, the cycle time and the blank time have the following relationships.

[amount of fluid discharged by pump per cycle]=
  [amount of substitution fluid per cycle]+[amount
  of removed water per cycle]

[amount of removed water per cycle]=[amount of
  water removed from patient]÷[number of cycles]

[number of cycles]=[working time]÷[cycle time]

[cycle time]={[time of filtration]+[time of filtration×
  time ratio of filtration to back-filtration]+[blank
  time]}

If the time ratio of filtration to back-filtration, the filtration rate and the back-filtration rate are fixed while those relationships are maintained to increase or reduce the time of back-filtration (the time of the back-filtration phase) per cycle, the time of filtration per cycle, the amount of the substitution fluid (stroke volume) and the amount of the fluid discharged by the pump are automatically set in connection to one another based on the above change.

When the time of filtration (the time of the filtration phase) is changed and also when the amount of the substitution fluid (stroke volume) is changed, other parameters are automatically set in connection to one another while the above relationships are maintained.

The filtration rate and the back-filtration rate are used as fixed parameters in the above case. However, the amount of the substitution fluid (stroke volume) can be set automatically as a fixed parameter.

When the filtration/back-filtration pattern per cycle is set or changed, the single-needle HDF apparatus according to the present invention has the function of setting the filtration/back-filtration pattern for each cycle after the set cycle to the same pattern.

When the single-needle HDF apparatus according to the present invention is coupled with hematocrit value measuring means, water removing conditions can be automatically changed by feeding back the state of blood from the hematocrit value measuring means.

Hereinafter, one embodiment mode of the present invention will be described with reference to the accompanying drawings. FIG. 1 is a schematic diagram of the whole hemodiafiltration apparatus of the present invention. The hemodiafiltration apparatus comprises a hemodialyzer 8 for purifying blood by contacting blood with a dialysis fluid through a porous membrane, a first blood circuit 10 having a blood pump P1 for introducing the blood taken out from a living body 9 into the dialyzer, a second blood circuit 11 having means for introducing the blood flowing out from the hemodialyzer into the living body, a dialysis fluid supply circuit 12 having a dialysis fluid supply pump P2 for introducing a dialysis fluid into the dialyzer 8, and a dialysis fluid discharge circuit 13 having a dialysis fluid discharge pump P3 for discharging the dialysis fluid flowing out from the hemodialyzer. A one puncture needle 17 communicates with the first blood circuit 10 and second blood circuit 11 though the junction portion of the needle 18. To achieve improved purification of the dialysis fluid, an endotoxin filter 16 is desirably provided in the dialysis fluid supply circuit 12 on the upstream side of the hemodialyzer 8.

In the hemodiafiltration apparatus 1, bypass circuits 14 and 15 having filtration/back-filtration fluid supply means or water removing and fluid discharge means P4/P5 which differs from the pump are provided in either one or both of the dialysis fluid supply pump installation portion of the above dialysis fluid supply circuit 12 and the dialysis fluid discharge pump installation portion of the dialysis fluid discharge circuit 13, and the water removing and fluid discharge means P4 and the filtration/back-filtration fluid supply means P5 provided in the bypass circuits 14 and 15 and the above blood pump P1 can turn in normal and opposite directions.

When the water removing and fluid discharge means P4 is turned in the same direction as the dialysis fluid discharge pump P3, water is removed by filtration and when the water removing and fluid discharge means P4 is turned in a direction opposite to that of the dialysis fluid discharge pump P3, the substitution fluid is injected by back-filtration. Or when the filtration/back-filtration fluid supply means P5 is turned in the same direction as the dialysis fluid supply pump P2, the substitution fluid is injected by back-filtration and when the filtration/back-filtration fluid supply means P5 is turned in a direction opposite to that of the dialysis fluid supply pump P2, water is removed by filtration.

Working devices 2 such as the blood pump P1, the pump of one or both of the above filtration/back-filtration fluid supply means and the water removing and fluid discharge means P4 and P5 (provided in the bypass circuits) and unshown channel opening/closing means for opening and closing the dialysis fluid circuit and the blood circuit are connected to control units 3 by transmission systems 7. The control units 3 activate one or both of the filtration/back-filtration fluid supply means and the water removing and fluid discharge means P4 and P5 to carry out forced back-filtration through the hemodialyzer 8.

A predetermined time after the dialysis fluid is flown into the blood side circuit by this back-filtration operation, the filtration/back-filtration fluid supply means P5 or the water removing and fluid discharge means P4 is activated to carry out filtration through the hemodialyzer 8. The fluid in the blood circuit is removed to the dialysis fluid side by this filtration operation. At this point, the amount of the fluid to be discharged is set so that the filtration/back-filtration fluid supply means P5 or the water removing and fluid discharge means P4 discharges the amount of a fluid obtained by adding the amount of water removed from the patient to the amount of the reversely filtered fluid (substitution fluid) flown previously.

Figure 2:
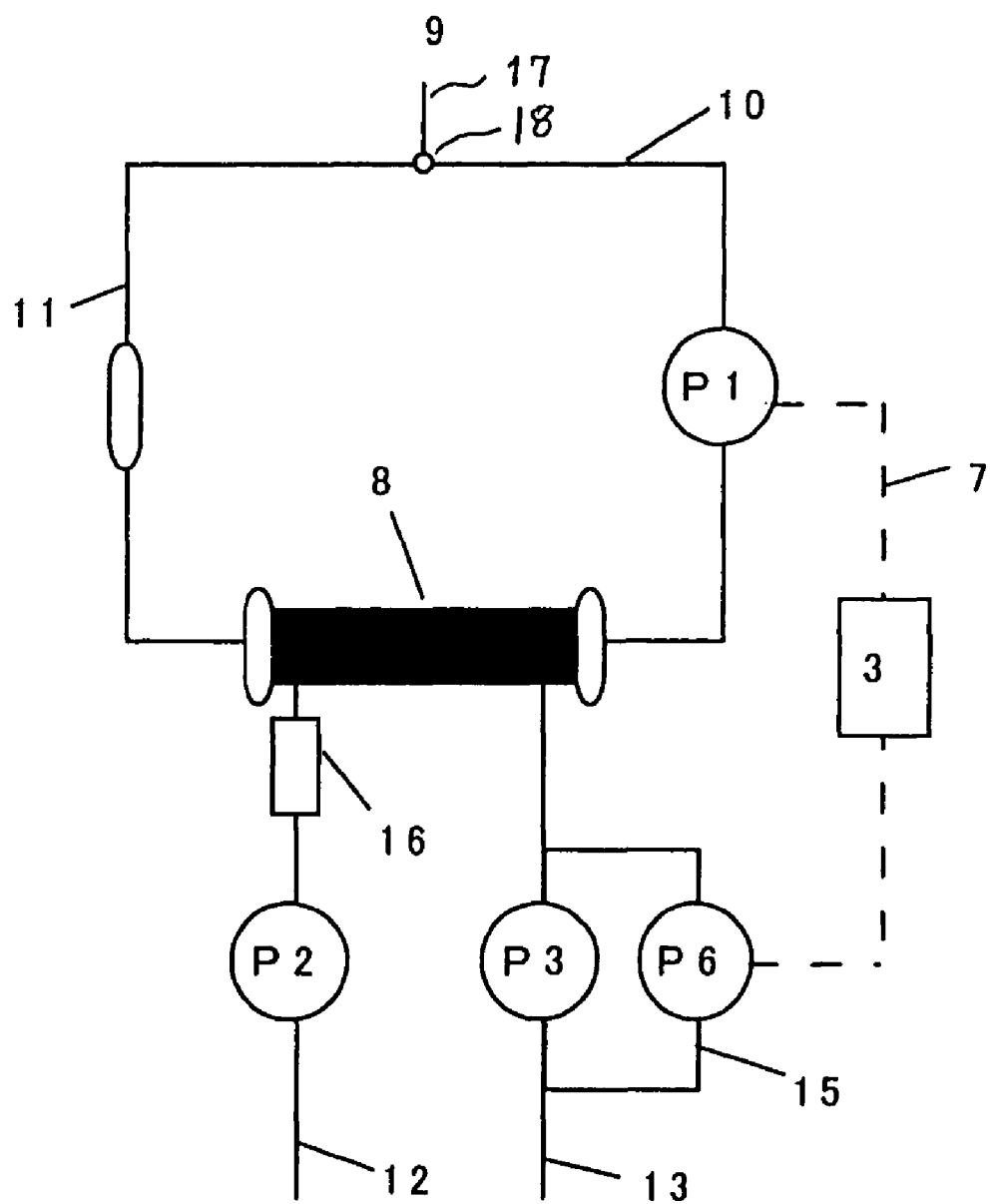
FIG. 2 is a schematic diagram of a hemodiafiltration apparatus utilizing multifunctional filtration control means according to an example of the present invention.

In an example shown in FIG. 2, filtration/back-filtration are controlled by the multifunctional filtration control means which can turn in normal and opposite directions and is provided in the bypass line of the dialysis fluid discharge line. That is, when the multifunctional filtration control means P6 is turned in the same direction as that of the dialysis fluid discharge pump P3, water is removed by filtration and when the multifunctional filtration control means P6 is turned in a direction opposite to that of the dialysis fluid discharge pump P3, the substitution fluid is injected by back-filtration.

The multifunctional filtration control means may be installed in the bypass line of the dialysis fluid supply line.

Figure 3:
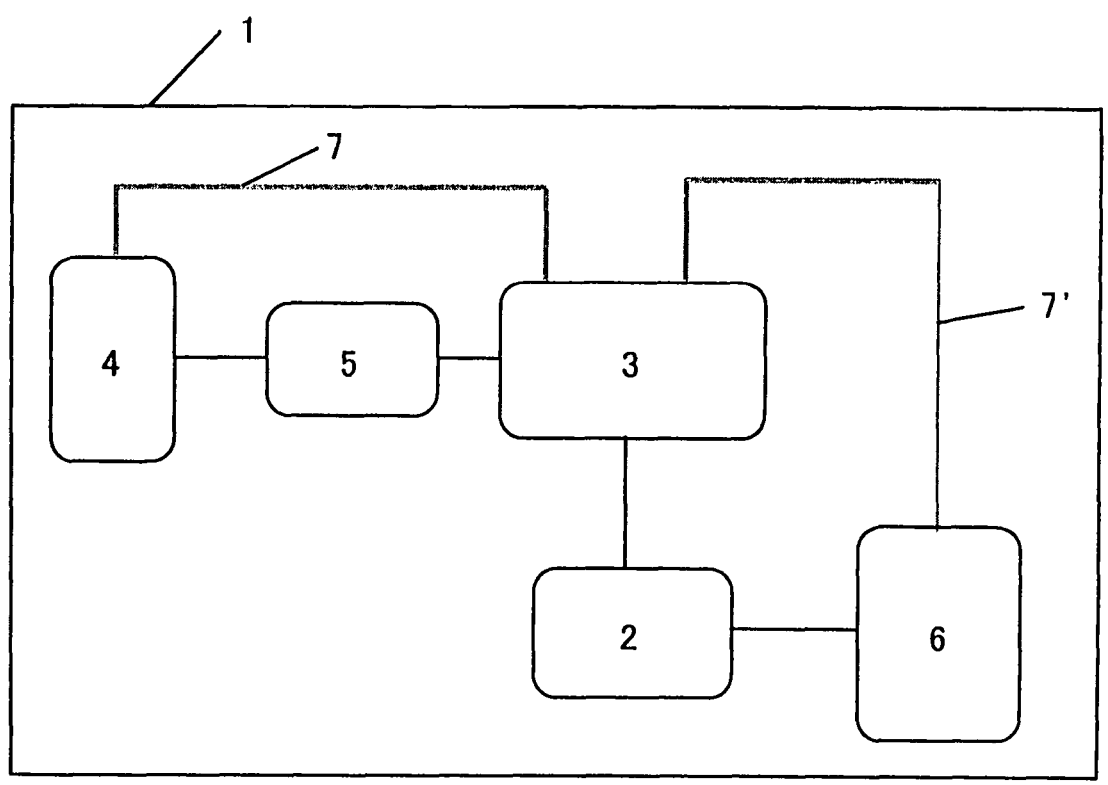
FIG. 3 is a flow chart schematically showing the flow of the processing/operation of a hemodiafiltration apparatus according to an example of the present invention.

FIG. 3 is a block diagram showing the construction of an embodiment of the hemodiafiltration apparatus of the present invention. The hemodiafiltration apparatus 1 of the embodiment shown in FIG. 3 includes a dialysis working device 2, a control unit 3 for controlling the operation and processing of the dialysis working device, an input unit 4 for inputting instructions/conditions and operation, a display unit 5 for displaying an input state and control mechanism, and a working device monitor 6 showing the operation state of the control unit. Transmission system 7 connects the control unit to the monitor 6, input unit 4, and as shown, indirectly to the other components.

The above input unit 4 and the working device monitor 6 are connected to the control unit 3 by transmission systems 7 to enable the conditions to be changed by the input unit 4 while the operation state of the dialysis working device 2 is confirmed on the monitor 6 and the operation of the dialysis working device 2 to be changed through the transmission systems 7 and the control unit 3. In FIG. 3, the input unit 4 and the working device monitor 6 are connected to the control unit 3 by the transmission systems 7 and 7. However, all of the above input unit 4, the monitor 6 and the control unit 3 may be connected to the transmission system 7.

Although not shown, the dialysis working device 2 is a device which is activated to carry out actual hemodiafiltration, such as unshown water removing and fluid discharge means, blood pump, dialysis fluid supply or discharge unit, channel opening and closing unit for opening and closing a fluid path such as a dialysis fluid circuit or blood circuit, and hemodialyzer for carrying out filtration or back-filtration.

The input unit 4 for inputting processing conditions and instructions is a device for setting or changing the amount of water removed from a patient, the working time of hemodiafiltration processing and the amount of the reversely filtered fluid flowing into the body of the patient, a device for setting or changing the time required for one cycle when one cycle is composed of water removal and the supplement of a fluid (by back-filtration), or the like. Preferably, these conditions can be input and changed from one panel but the present invention is not limited to this.

The display unit 5 from which an operator checks (confirms) the instructions and conditions of the above input unit 4, their input states and control mechanism before the start of the working device may be composed of a panel integrated with the input unit. As described above, the monitor 6 for monitoring the operation state of the dialysis working device 2 is connected to the working device 2, displays the operation state of the working device 2 and can adjust the working device 2 finely through the transmission systems 7 and 7 and the control unit 3 when the working device does not operate according to the preset conditions.

Figure 4:
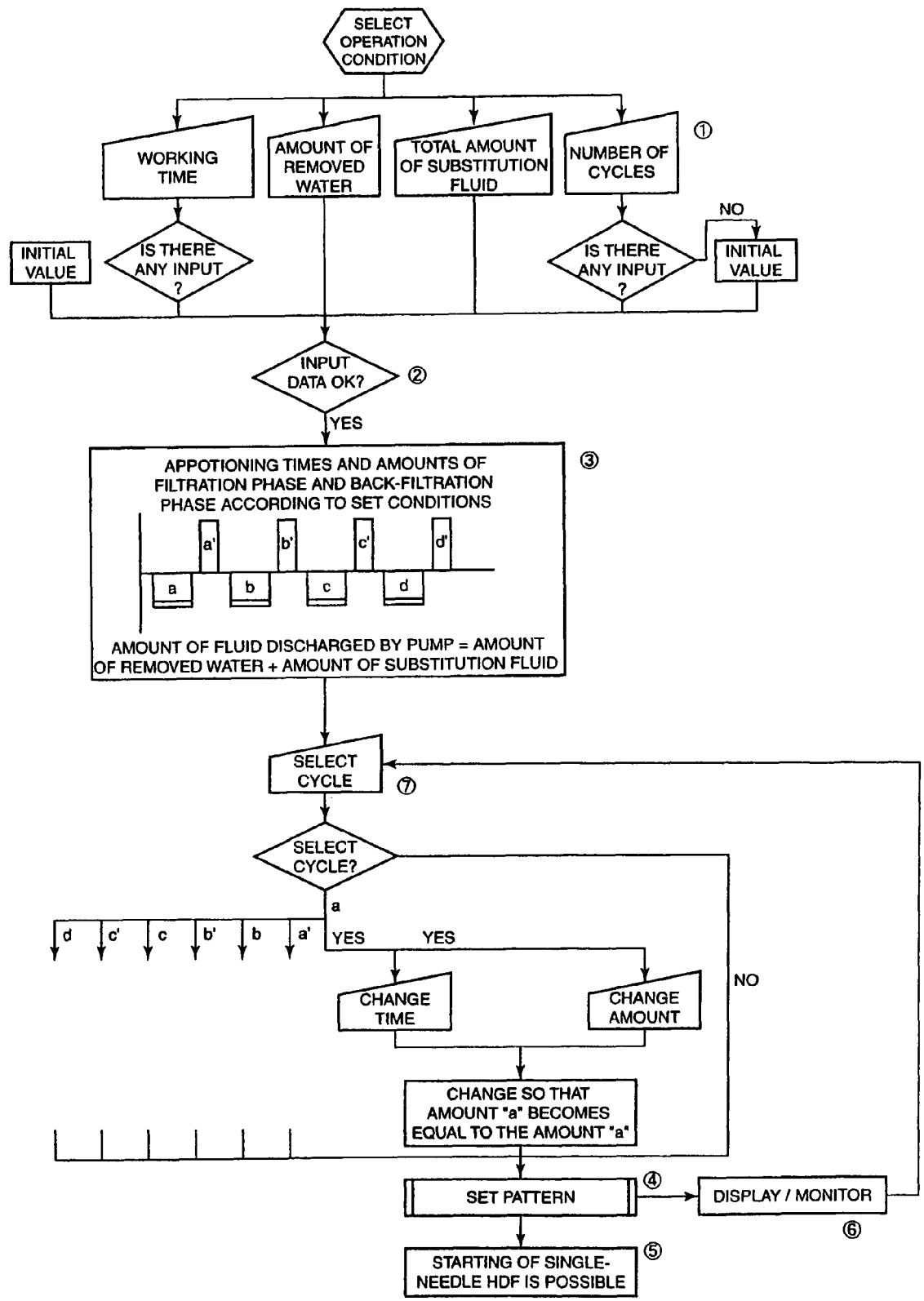
FIG. 4 is a block diagram showing a schematic construction of an embodiment of the hemodiafiltration apparatus of the present invention.

FIG. 4 is a flow chart showing a procedure for carrying out the hemodiafiltration process by means of the hemodiafiltration apparatus of the present invention, that is, all the steps including (1) the setting of conditions (input), (2) the confirmation of inputs, (3) the display of hemodiafiltration conditions, (4) confirmation and determination, (5) execution (hemodiafiltration process), (6) the monitoring of the operation state of the dialysis working device, (7) adjustment and alteration, and (8) feedback control to the dialysis working device.

The amount of the removed water, the working time and the total amount of the substitution fluid (the amount of the reversely filtered fluid flowing into the body of the patient) are first set and input into the input unit 4. How many cycles, each cycle composed of the injection of the substitution fluid from the hemodialyzer by back-filtration and the removal of water by filtration, are carried out in the time during which hemodiafiltration is carried out is set. Since the working time per cycle is the time during which hemodiafiltration is carried out in each cycle, the time may be set. For example, the working time per cycle can be adjusted to a range from 1 minute to 60 minutes.

If input restrictions are set in the hemodiafiltration apparatus so that the relationship between the time of injecting the substitution fluid by back-filtration (the time of the back-filtration phase) and the time of the filtration phase for carrying out the filtration operation always becomes [time of back-filtration phase]<[time of filtration phase], the removal of the solute or the purification of the blood can be carried out efficiently without applying stress to the living body. If input restrictions are set in the hemodiafiltration apparatus to satisfy [total amount of substitution fluid]+[amount of water removed from patient]=[total amount of fluid discharged by pump], the amount of a fluid discharged by the water removing and fluid discharge means is calculated automatically by setting the total amount of the substitution fluid and the amount of water removed from the patient, and the water removing and fluid discharge means is controlled, which is convenient.

Figure 5:
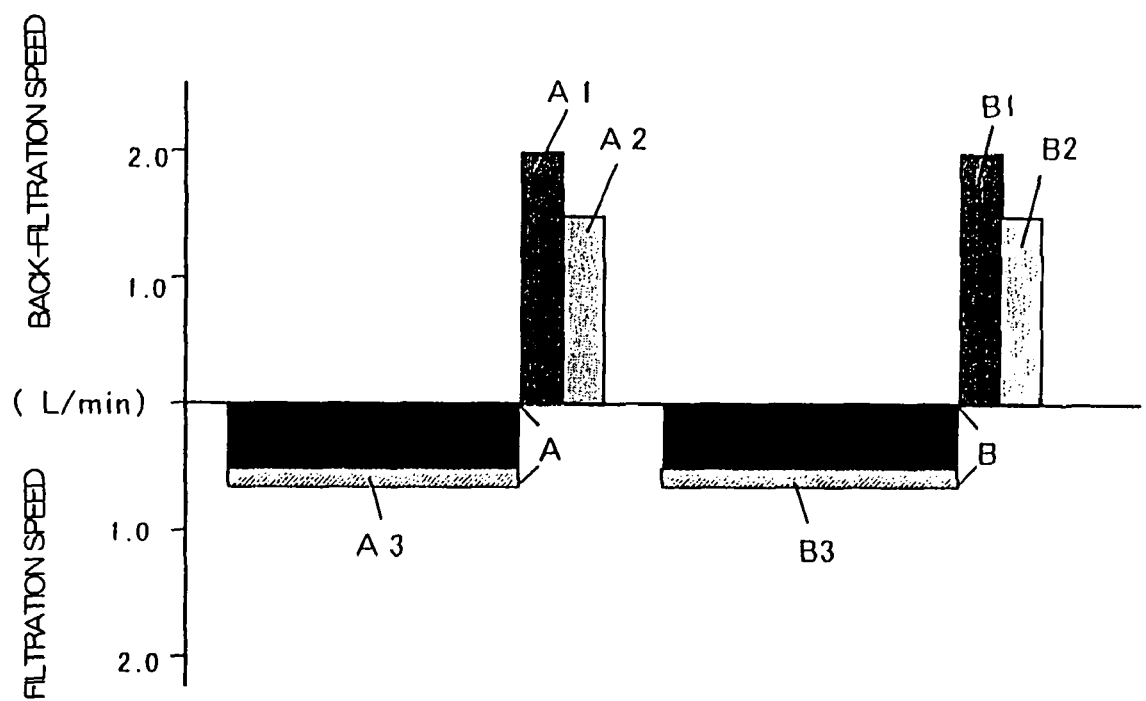
FIG. 5 is a schematic diagram of an example of a filtration/back-filtration pattern performed by the hemodiafiltration apparatus of the present invention.

As for the input operation of the hemodiafiltration apparatus, as shown in FIG. 4, when the amount of water removed from the patient and the total amount of the substitution fluid are not input, the routine cannot proceed to the next step. However, when the working time and the number of cycles are not input, default values (initial values) are already set and therefore, the operation is controlled with the initial values. After a picture for confirming whether values to be set are input or not is displayed and the values are confirmed, a pattern which is composed of the amount of the substitution fluid, the amount of water removed from the patient per cycle and the amount of a fluid discharged by a water removing pump as shown in FIG. 5 is displayed.

When A denotes the amount of the fluid discharged by the water removing pump in the first cycle, A1 the amount of the first substitution fluid in the first cycle, A2 the amount of the second substitution fluid in the first cycle, A3 the amount of water removed from the patient in the first cycle, B the amount of the fluid discharged by the water removing pump in the second cycle, B1 the amount of the first substitution fluid in the second cycle, B2 the amount of the second substitution fluid in the second cycle, and B3 the amount of water removed from the patient in the second cycle, the amount of water removed from the patient, the working time, the total amount of the substitution fluid and the time of the back-filtration phase can be set and changed while the relationships A=A1+A2+A3 and B=B1+B2+B3 are maintained.

The working pattern which is actually carried out is changed by the following procedure. By determining (inputting) the amount of the removed water, the working time, the total amount of the substitution fluid and the number of cycles, the cycle time and the time of the filtration phase required per cycle are automatically calculated. As a result, [time of filtration phase/cycle]=[cycle time]−[time of filtration phase/cycle]−[time of blank phase/cycle]−[time of blood circulation step/cycle] is set on the screen.

On this screen, [working time/cycle], the amount of the fluid discharged by the water removing pump and the back-filtration rate are determined by changing [time of back-filtration phase/cycle] while maintaining the above-mentioned relationship (that the sum of the amount of the substitution fluid and the amount of water removed from the patient becomes equal to the amount of the fluid discharged by the water removing pump). On the contrary, [time of back-filtration phase/cycle] may be changed by altering and setting [working time/cycle].

By changing the cycle time and [total amount of substitution fluid/cycle], the amount of the substitution fluid can be changed for each cycle. The total time of all the cycles can also be changed. Changes in the amount of the substitution fluid and the time are reflected on the subsequent cycles. By changing the pattern per cycle, the remaining cycle patterns are changed to the same pattern as above, or each pattern can be set.

Further, the amount of water removed from the patient can also be changed for each cycle according to a water removing pattern obtained by a hematocrit monitor for measuring the hematocrit value and ultrafiltration.

Since the single-needle HDF of the present invention may cause blood concentration in the hemodialyzer depending on the amount of filtration by filtration operation, warning standard values of venous pressure and dialysis fluid pressure and a TMP warning value are desirably set separately.

Embodiment 1

As the single-needle HDF according to the present invention, an embodiment of single-needle HDF of a type in which the amount of filtration (equal to the amount of the substitution fluid) per cycle (hereinafter referred to as "stroke volume (SV)") is relatively small at 50 ml is shown.

First, the construction of the single-needle HDF apparatus is shown. The blood circuit used in the apparatus is a blood circuit for a single needle and has a junction portion with a Y-shaped or T-shaped puncture needle, two branch circuits branching off from the junction portion and a pump segment for mounting a blood pump to one of the branch circuits. In this embodiment, the branch having the pump segment is used as a branch on the arterial side (blood circuit). The single-needle HDF apparatus according to this embodiment has a blood pump (which may turn only in a normal direction) as a mechanism for a blood supply system and the above blood circuit for a single needle is mounted to the mechanism. The apparatus has a dialysis fluid supply line for perfusing the hemodialyzer with the dialysis fluid as a dialysis fluid supply system, and the dialysis fluid supply line and the dialysis fluid discharge line are provided with delivery means for supplying the dialysis fluid and delivery means for discharging the dialysis fluid, respectively. Further, as a system for controlling the movement of the fluid between two supply systems which are a blood supply system and a dialysis fluid supply system, the dialysis fluid supply line is provided with one filtration/back-filtration fluid supply means capable of controlling the flow rate, which can turn both in normal and opposite directions to carry out filtration (extraction of blood) and back-filtration (reinfusion), and the dialysis fluid discharge line is provided with water removing and fluid discharge means. The filtration/back-filtration fluid supply means, the water removing and fluid discharge means and the blood pump can be controlled in an associated manner. The cycle time, SV, the time ratio of the filtration phase per cycle (one time or more), back-filtration phase per cycle (one time or more) and blank phase per cycle (0, one or more times), the filtration rate and the back-filtration rate are freely controlled by the single-need HDF apparatus so that a desired filtration/back-filtration pattern can be set.

In the single-needle HDF apparatus according to this example, SV is set to 50 ml, the cycle time to 30 seconds, the time of the filtration phase to 15 seconds, the time of the first blank phase between the filtration phase and the back-filtration phase to 1/16 minute (3.75 seconds), the time of the back-filtration phase to 1/8 minute (7.5 seconds), and the time of the second blank time between the back-filtration phase and the filtration phase to 1/16 minute (3.75 seconds). The filtration rate in the filtration phase is 200 ml/min, and the back-filtration rate in the back-filtration phase is 400 ml/min. The blood pump is coupled with each phase and supplies the blood at a rate of 200 ml/min in the filtration phase, 400 ml/min in the first blank phase, stops in the back-filtration phase, and supplies the blood at a rate of 400 ml/min in the second blank time. The working time is 4 hours during which the cycle is repeated in the same filtration/back-filtration pattern.

In the filtration phase which lasts 15 seconds, the blood is removed from the body of the patient by the blood pump at a rate of 200 ml/min until 50 ml is obtained, and the filtration/back-filtration fluid supply means is turned synchronously in the normal direction (direction opposite to that of the dialysis fluid supply pump) at a rate of 200 ml/min until an SV of 50 ml is reached. The physical principle of blood purification in the filtration phase is HDF, that is, filtration and diffusion by the perfusion of the dialysis fluid.

In the first blank phase which lasts 3.75 seconds, the filtration/back-filtration fluid supply means stops, and recirculation is driven by the blood pump at a rate of 400 ml/min. The physical principle of blood purification in the first blank phase is HD, that is, diffusion by the counterflows of the blood and the dialysis fluid.

In the back-filtration phase which lasts 7.5 seconds, the blood pump stops, and the filtration/back-filtration fluid supply means is turned in the opposite direction at a rate of 400 ml/min until an SV of 50 ml is reached. The back-filtration dialysis fluid moves through the hemodialyzer and the blood circuit on the venous side, whereby 50 ml of the blood is returned to the body of the patient.

In the second blank phase which lasts 3.75 seconds, the filtration/back-filtration fluid supply means stops, and recirculation is driven by the blood pump at a rate of 400 ml/min. The physical principle of blood purification in the second blank phase is HD, that is, diffusion by the counterflows of the blood and the dialysis fluid. Single-needle HDF treatment is continued while blood extraction and reinfusion and capacity balance between filtration and back-filtration are attained in each cycle composed of four phases.

When the water removing and fluid discharge means is activated continuously independently, water removal is carried out at a fixed rate regardless of the four phases so that a predetermined amount of water can be removed in the working time.

The solute removal efficiency before and after treatment by single-needle HDF according to this embodiment was compared with that of HD which uses two ordinary puncture needle for the same blood current. The single-needle HDF showed a removal efficiency for urea (60 Dalton) which is a small molecule, that is, ({concentration before treatment−concentration after treatment}/concentration before treatment) of about 70% of that of ordinary HD. On the other hand, the removal efficiency for β2-microglobulin (11,800 Dalton) which is a large molecule was high at about 150% of that of ordinary HD. The albumin loss was reduced to a small value.

It can be concluded that the treatment efficiency is in an almost allowable range for small molecules and excellent for large molecules.

Embodiment 2

As the single-needle HDF according to the present invention, an embodiment of single-needle HDF of a variation in which the SV is very small at 200 ml is shown.

First, the construction of the single-needle HDF apparatus according to Embodiment 2 is shown. The blood circuit used in the apparatus is a blood circuit for a single needle and has a junction portion with a Y-shaped puncture needle, two branch circuits branching off from the junction portion and a pump segment for mounting a blood pump to one of the branch circuits. In this embodiment, the branch having the pump segment is used as a branch on the arterial side (blood circuit). The single-needle HDF apparatus according to this embodiment has a blood pump which can turn both in normal and opposite directions as a mechanism for a blood supply system and the above blood circuit for a single needle is mounted to the mechanism. The apparatus has a dialysis fluid supply line for perfusing the dialyzer with the dialysis fluid as a dialysis fluid supply system, and the dialysis fluid supply line and the dialysis fluid discharge line are provided with delivery means for supplying the dialysis fluid and delivery means for discharging the dialysis fluid, respectively. Further, as a system for controlling the movement of the fluid between two supply systems which are a blood supply system and a dialysis fluid supply system, the dialysis fluid supply line is provided with one filtration/back-filtration fluid supply means capable of controlling the flow rate, which can turn both in normal and opposite directions to carry out filtration (extraction of blood) and back-filtration (reinfusion), and the dialysis fluid discharge line is provided with water removing and fluid discharge means. The filtration/back-filtration fluid supply means, the water removing and fluid discharge means and the blood pump can be controlled in an associated manner. The cycle time, SV, the time ratio of the filtration phase per cycle (one time or more), back-filtration phase per cycle (one time or more) and blank phase per cycle (0 or more times), the filtration rate and the back-filtration rate are freely controlled by the single-need HDF apparatus so that a desired filtration/back-filtration pattern can be set.

In the single-needle HDF apparatus according to this example, SV is set to 200 ml, the cycle time to 120 seconds, the time of the first filtration phase to 30 seconds, the time of the second filtration phase (filtration circulation phase) to 60 seconds, and the time of the back-filtration phase to 30 seconds. The filtration rate in the first filtration phase is 400 ml/min, the filtration rate in the second filtration phase is 100 ml/min, and the back-filtration rate in the back-filtration phase is 600 ml/min. The blood pump is coupled with each phase and has a supply rate of 200 ml/min in the first filtration phase, 400 ml/min in the second filtration phase and 300 ml/min in the opposite direction in the back-filtration phase. The working time is 4 hours during which the cycle is repeated in the same filtration/back-filtration pattern.

In the first filtration phase which lasts 30 seconds, the filtration/back-filtration fluid supply means turns in the normal direction for filtration at a rate of 400 ml/min, and the blood pump removes the blood from the blood circuit on the arterial side at a rate of 200 ml/min. Therefore, the amount of the blood corresponding to a flow rate of 200 ml/min which is the difference between them is removed in the direction of the hemodialyzer through the blood circuit on the venous side. The physical principle of blood purification in the filtration phase is HDF, that is, filtration and diffusion by the perfusion of the dialysis fluid.

In the second filtration phase which lasts 60 seconds, slower filtration and re-circulation than in the first filtration phase are carried out. The filtration/back-filtration fluid supply means turns in the normal direction for filtration at a rate of 100 ml/min, and the blood pump turns in the normal direction at a rate of 400 ml/min. Therefore, the blood is removed from the body of the patient at a rate of 100 ml/min while it re-circulates in the blood circuit in the normal direction of the blood pump at a rate of 300 ml/min. The physical principle of blood purification in the second filtration phase is HDF, that is, filtration and diffusion by the perfusion of the dialysis fluid.

In the back-filtration phase which lasts 30 seconds, the filtration/back-filtration fluid supply means turns in the opposite direction to drive quick back-filtration at a rate of 600 ml/min, and the blood pump turns in the opposite direction at a rate of 300 ml/min. Therefore, the amount of the blood corresponding to a flow rate of 300 ml/min which is the difference between them is returned to the body through the blood circuit on the venous side. The back-filtration ends when an SV of 200 ml is reached. Single-needle HDF treatment is continued while blood extraction and reinfusion and capacity balance between filtration and back-filtration is attained in each cycle composed of three phases.

When the water removing and fluid discharge means is activated continuously independently, water removal is carried out at a fixed rate regardless of the three phases so that a predetermined amount of water can be removed in the working time.

By using single-needle HDF according to this embodiment, a removal efficiency for urea which is a small molecule is about 70% of that of ordinary HD. On the other hand, the removal efficiency for β2-microglobulin which is a large molecule is high at about 180% of that of ordinary HD. The albumin loss is larger than that of Embodiment 1. It can be concluded that the treatment efficiency is superior as compared to Embodiment 1, in an allowable range for small molecules and very excellent for large molecules.

As shown in the above two embodiments, the single-needle HDF apparatus according to the present invention is characterized in that it combines a plurality of phases arbitrarily in one cycle and couples the filtration/back-filtration fluid supply means with the blood pump to control the flow rate in the normal direction and opposite direction or to stop them, thereby making it possible to create various filtration/back-filtration patterns.

INDUSTRIAL APPLICABILITY

Since the removal of urotoxin is effected in a well-balanced manner from small to large molecules by using a hemodiafiltration apparatus making use of a single-needle extracorporeal circulation circuit according to the present invention, though there is only one puncture needle for blood access, the efficiency of this single-needle blood purification method is much higher than that of the prior art, it can be said that the clinical application of the hemodiafiltration apparatus is made possible for the first time as means for treating chronic renal failure. The removal efficiency of urea reaches 60 to 80% of that of ordinary HD which uses two puncture needles and the removal performance of small molecules falls within a tolerable range from the viewpoint of urea kinetics. The removal of medium and high molecular weight substances is improved by the effect of filtration, and the removal efficiency of large molecules is much higher than that of ordinary HD. Since filtration/back-filtration conditions can be set arbitrarily, when appropriate conditions are selected, even if a dialysis membrane having a large hole diameter is used, the albumin loss can be reduced to an appropriate value. As a patient suffering from renal failure gets older, his/her blood vessels become thinner and more fragile. Therefore, it is considered that the number of cases where blood access is difficult will continue to increase from now on, and it can be said that the single-needle HDF according to the present invention is suitable for those cases.

The invention claimed is:

1. A hemodiafiltration apparatus for performing extraction and reinfusion of blood alternately and intermittently by using one puncture needle, comprising:
    a hemodialyzer in which blood and a dialysis fluid are brought into contact with each other through a porous membrane to purify blood;
    an arterial side blood circuit in communication with a patient via said one puncture needle and in communication with the hemodialyzer:
    a venous side blood circuit in communication with the patient via said one puncture needle and in communication with the hemodialyzer;
    wherein the arterial side blood circuit, the venous side blood circuit, and a first side of the hemodialyzer comprise a patient side of the apparatus;
    a dialysis fluid supply line through which a dialysis fluid is supplied to the hemodialyzer;
    a dialysis fluid discharge line through which the dialysis fluid is discharged from the hemodialyzer;
    a blood pump provided in one of the arterial side blood circuit and the venous side blood circuit, the blood pump providing a blood flow at a preselected flow rate and operable in a normal direction and an opposite direction;
    a supply delivery means for supplying the dialysis fluid provided in the dialysis fluid supply line;
    a discharge delivery means for discharging the dialysis fluid provided in the dialysis fluid discharge line;
    a filtration/back-filtration fluid supply means provided in parallel with the supply delivery means for supplying the dialysis fluid, the filtration/back-filtration fluid supply means operable in normal and opposite directions, the filtration/back-filtration fluid supply means providing a flow of fluid in the hemodialyzer at a preselected flow rate;
    wherein the dialysis fluid supply line, the dialysis fluid discharge line; the supply delivery means, the discharge delivery means, and the filtration/back-filtration fluid supply means comprise a hemodialysis side of the apparatus; and
    a control means for controlling the filtration/back-filtration fluid supply means by issuing a series of instructions to the filtration/back-filtration fluid supply means, the series of instructions comprising a cycle repeated a predetermined number of times, the instructions including: an instruction directing the filtration/back-filtration fluid supply means to operate in a flow direction opposite to a flow direction of a supply delivery means for supplying the dialysis fluid for a preset, predetermined period of time to perform the extraction of blood from the body of the patient; an instruction directing the filtration/back-filtration fluid supply means to stop operating for a preset, predetermined period of time to purify blood through diffusion by counterflow with the dialysis fluid; an instruction directing the filtration/back-filtration fluid supply means to operate in a flow direction that is the same as a flow direction of the supply delivery means for supplying the dialysis fluid for a preset, predetermined period of time that is shorter than the period of time for the extraction of blood to perform a reinfusion of blood to the body of the patient; and an instruction directing the filtration/back-filtration fluid supply means to stop operating for a preset, predetermined period of time to purify blood through diffusion by a counterflow with the dialysis fluid.

2. A hemodiafiltration apparatus according to claim 1, wherein the one puncture needle comprises a Y-shaped or T-shaped junction portion and a puncture needle, the Y-shaped or T-shaped junction portion having a first branch in communication with the arterial side blood circuit and a second branch in communication with the venous side blood circuit, the arterial side branch circuit positioned on an upstream side of the hemodialyzer and the venous side branch circuit positioned on a downstream side of the hemodialyzer.

3. A hemodiafiltration apparatus according to claim 2, wherein the flow rate of blood in the hemodialyzer is equal to a blood filtration rate in the hemodialyzer.

4. A hemodiafiltration apparatus according to claim 2, wherein the blood is returned to the patient by adjusting the fluid supply rate from the hemodialyzer side to the patient side to be equal to the back-filtration flow rate on the hemodialyzer side.

5. A hemodiafiltration apparatus according to claim 2, wherein the blood pump is stopped and back-filtration is performed, whereby back-filtration effects return of blood to the patient side.

6. The hemodiafiltration apparatus according to claim 2, wherein an amount of blood corresponding to a difference between the blood flow rate provided by the blood pump and a filtration rate is re-circulated from the one of the arterial side blood circuit and the venous side blood circuit where the blood pump is not provided to the other of the arterial side blood circuit and the venous side blood circuit where the blood pump is provided.

7. The hemodiafiltration apparatus according to claim 1, wherein the blood is returned to the patient side based on the ratio of the fluid supply rate to the patient side from the hemodialyzer side to the back-filtration rate in the hemodialyzer during the back-filtration operation.

8. The hemodiafiltration apparatus according to claim 1, wherein each of the blood flow rate, filtration rate, and back-filtration rate is determined by the product of flow rate times the period of fluid flow.

9. The hemodiafiltration apparatus according to claim 1, further comprising multifunctional filtration control means for control of filtration/back-filtration rates, and the duration of each of a filtration phase, a back-filtration phase and a blank phase during which blank phase neither a filtration operation nor a back-filtration operation are carried out.

10. The hemodiafiltration apparatus according to claim 1, wherein the control means further controls the blood pump, and in association with the instruction directing the filtration/back-filtration fluid supply means to operate in a flow direction opposite to a flow direction of a supply delivery means for supplying the dialysis fluid for a preset, predetermined period of time to perform the extraction of blood from the body of the patient, the control means issues an instruction to the blood pump controlling the flow rate of the blood and the control means issues a further instruction to filtration/back-filtration fluid supply means controlling the rate of fluid supplied by the filtration/back-filtration fluid supply means, whereby a relationship between a filtration rate and the flow rate of blood is established, which further provides for selection of a channel for blood flow through one of the arterial side blood circuit and the venous side blood circuit.

11. The hemodiafiltration apparatus according to claim 1, wherein the control means further controls the blood pump, and in association with the instruction directing the filtration/back-filtration fluid supply means to operate in a flow direction opposite to a flow direction of a supply delivery means for supplying the dialysis fluid for a preset, predetermined period of time to perform the extraction of blood from the body of the patient, the control means issues an instruction to the filtration/back-filtration fluid supply means directing that the rate of fluid supplied by the filtration/back-filtration fluid supply means be greater than the rate of fluid supplied by the blood pump, whereby blood is extracted from the patient using the arterial side blood circuit as a first channel and blood is extracted from the patient blood using the venous side blood circuit as a second channel that is in parallel to the first channel.

12. The hemodiafiltration apparatus according to claim 1, wherein the control means further controls the blood pump, and, wherein, in association with the instruction directing the instruction directing the filtration/back-filtration fluid supply means to operate in a flow direction that is the same as a flow direction of the supply delivery means for supplying the dialysis fluid for a preset, predetermined period of time that is shorter than the period of time for the extraction of blood to perform the reinfusion of blood in the body of the patient, the control means issues an instruction to the blood pump controlling the blood flow rate and the control means issues an instruction to the filtration/back-filtration fluid supply means controlling the filtration/back-filtration fluid flow rate, whereby a relationship between a back filtration rate and the blood blow rate is established, further providing for selection of a channel for blood flow.

13. The hemodiafiltration apparatus according to claim 1, wherein the control means further controls the blood pump, and in association with the instruction directing the filtration/back-filtration fluid supply means to operate in a flow direction that is the same as a flow direction of the supply delivery means for supplying the dialysis fluid for a preset, predetermined period of time that is shorter than the period of time for the extraction of blood to perform the reinfusion of blood in the body of the patient, the control means issues an instruction to the filtration/back-filtration fluid supply means directing that the rate of fluid supplied by the filtration/back-filtration fluid supply means be greater than the rate of fluid supplied by the blood pump, whereby the patient is reinfused with blood using the arterial side blood circuit as a first channel and the patient is reinfused with blood using the venous side blood circuit as a second channel that is parallel to the first channel.

14. A hemodiafiltration apparatus according to claim 1, further comprising a water removing means and fluid discharge means provided in the dialysis fluid discharge line.

15. The hemodiafiltration apparatus according to claim 14, wherein water is removed from the blood, the water removal carried out by activating the water removing means and fluid discharge means in one or more of a filtration phase, a back-filtration phase and a blank phase during which blank phase neither a filtration operation nor a back-filtration operation are carried out.

16. The hemodiafiltration apparatus according to claim 15, wherein the removal of water includes maintaining a volume of fluid on the patient side constant by extracting the blood in an amount equal to an amount of the removed fluid from the patient side.

17. A hemodiafiltration apparatus according to claim 1, wherein the one puncture needle is or controlled by inputting an amount of removed water and a total amount of a substitution fluid, which is equal to the total amount of filtrate which flows out through the filtration operation.

* * * * *